United States Patent
Roessler (12)

(10) Patent No.: US 6,706,273 B1
(45) Date of Patent: Mar. 16, 2004

(54) COMPOSITION FOR IMPLANTATION INTO THE HUMAN AND ANIMAL BODY

(75) Inventor: Ralf Roessler, Wetzlar (DE)

(73) Assignee: Ivoclar Vivadent AG, Schaan (LI)

( * ) Notice: Subject to any disclaimer, the term of this patent is extended or adjusted under 35 U.S.C. 154(b) by 86 days.

(21) Appl. No.: 09/807,569

(22) PCT Filed: Aug. 14, 2000

(86) PCT No.: PCT/EP00/07915

§ 371 (c)(1),
(2), (4) Date: Apr. 13, 2001

(87) PCT Pub. No.: WO01/12242

PCT Pub. Date: Feb. 22, 2001

(30) Foreign Application Priority Data

Aug. 14, 1999 (DE) ......................................... 199 38 704

(51) Int. Cl.$^7$ .............................. A61F 13/00; A61F 2/00
(52) U.S. Cl. ....................... 424/422; 424/423; 424/426
(58) Field of Search ................................. 424/422, 423, 424/426

(56) References Cited

U.S. PATENT DOCUMENTS

| | | | | |
|---|---|---|---|---|
| 4,673,355 | A | 6/1987 | Farris et al. | ................. 433/218 |
| 5,053,212 | A | 10/1991 | Constantz et al. | ........... 423/305 |
| 5,262,166 | A | 11/1993 | Liu et al. | ..................... 424/423 |
| 5,820,632 | A | 10/1998 | Constantz et al. | ............. 623/16 |

FOREIGN PATENT DOCUMENTS

| | | | |
|---|---|---|---|
| DE | 41 32 331 A1 | | 4/1992 |
| EP | 0 520 693 A3 | | 12/1992 |
| EP | 0 543 765 | * | 5/1993 |
| EP | 0 543 765 A1 | | 5/1993 |
| EP | 0 664 133 A1 | | 7/1995 |
| EP | 1 002 513 A1 | | 5/2000 |
| EP | 1 002 513 | * | 5/2000 |
| FR | 2 772 746 | * | 6/1999 |
| GB | 2 260 977 A | | 5/1993 |
| WO | WO 99/17710 | * | 4/1999 |

OTHER PUBLICATIONS

Knabe et al Morphological evaluation of osteoblasts cultured on different calcium phosphate ceramics Biomaterial 18:1339–1347 1997.*

Berger et al Resorbable glass ceramics with controlled dissolution Vortr. Poster–Symp. Materialforschung 3:2621–2623 1991.*

Muller–Mai et al The bony reaction to rapidly degradable glass–ceramic based on the new phase Ca2KNa(PO4)2 Bioceramics 10:53–56 1997.*

Knabe et al., "In vitro Investigation of Novel Calcium Phosphates Using Osteogenic Cultures," *J. Materials Sci.: Materials in Medicine*, 9:337–345 (1998).

Martinez et al., "Identification of Functional Insulin–Like Growth Factor–II/Mannose–6–Phosphate Receptors in Isolated Bone Cells," *J. Cellular Biochem.*, 59:246–257.

Berger et al., "Resorbable Glass Ceramics with Controlled Dissolution,"Vortr. Poster–Symp. MaterialForschung. Bd 3, pp. 2621–2623 XP 000972626 (1991).

Driessen st al., "Amorphous Calcium Phosphate Cements and Their Transformation Into Calcium Hydroxyapatie," *Bioceramics*, 9:231–234 (1996).

Knabe et al., "Morphological Evaluation of Osteoblasts Cultured on Different Calcium Phosphate Ceramics," *Biomaterials*, 18:1339–1347 (1997).

Mëller–Mai et al., "The Bony Reaction to Rapidly Degradable Glass–Ceramics Based on The New Phase $Ca_2KNNa(PO_4)_2$," *Bioceramics,*10:53–56 (1997).

* cited by examiner

*Primary Examiner*—Thurman K. Page
*Assistant Examiner*—Amy E. Pulliam
(74) *Attorney, Agent, or Firm*—Nixon Peabody LLP

(57) ABSTRACT

Compositions for implantation into the human and animal body as bone replacement contain inter alia calcium and phosphorus and consist in particular of mixtures of powders and admixing liquids. They are suitable for preparing calcium phosphate cement pastes which cure at room and/or body temperature. The reaction systems contain a powdery base mixture comprising $CaKPO_4$, $Ca_2NaK(PO_4)_2$ and $Ca(H_2PO_4)_2 \cdot H_2O$.

18 Claims, No Drawings

COMPOSITION FOR IMPLANTATION INTO THE HUMAN AND ANIMAL BODY

The invention relates to compositions for implantation into the human and animal body.

These implantable compositions serve in particular for the replacement or repair of bones or teeth as well as parts thereof. They are particularly preferably used in the field of dentistry, i.e. in teeth and the bones of the masticatory apparatus, and therefore as dental materials. The compositions consist in particular of powder mixtures and admixing liquids, which are mixed directly before use, i.e. implantation, to form curing pastes. An essential part of the powder mixture comprises a powder of differing composition containing calcium phosphate. The admixing liquid is e.g. demineralized water or an aqueous solution, with the addition of substances, inter alia for improving the biological degradability and/or the acceleration of the tissue integration. Antibiotics and/or disinfectants can also be added to the compositions, to avoid infections.

The aim of the present invention is to avoid disadvantages which are present in the implantation systems for bone replacement corresponding to the state of the art. These disadvantages are as follows:

The following is disadvantageous when using bone implants made from solid material:

A costly adaptation involving the implant or the bone tissue is necessary in order that the hole to be filled in the bone tissue is completely closed.

When using implants which can be admixed to produce pastes, the previously mentioned disadvantage does not occur, but there are a series of other disadvantages, as follows:

The curing times of the admixed pastes are sometimes very short, which is a major hindrance during complicated operations. There are also pastes with very long curing times, which is also undesired.

After they are introduced into the bone tissue and before curing, the pastes are in part not resistant to liquids such as e.g. blood, i.e. they absorb liquid and soften.

The strength values of the cured pastes are sometimes low. In particular, the initial strength is in many cases too low.

In the paste-based implant materials which have become known, the rate at which the tissue integration and resorption occurs is only low.

Such implants are either not at all, or only slightly, biodegradable.

Details on this point emerge from the state of the art as described below:

The mineral bone material occurring in human and animal bodies consists predominantly of a hydroxyl apatite-like structure, the essentially occurring elements being calcium and phosphorous. Other elements also occur, however, in the bone substance, such as sodium, calcium, magnesium and barium.

The replacement of lost bone tissue by natural bone still presents considerable problems even today. This applies in particular in maxillofacial surgery, in accident surgery as well as in orthopaedics. These problems result from the limited availability of autologous bone or the great cost of procuring it, or the insufficient quality when using allogenic bone, combined with the risk of the transfer of diseases.

However, the synthetic bone replacement materials such as Bio-Oss®, Synthacer® or the bioglasses, which are available at present as a solid substance also have considerable disadvantages. These are e.g. that due to their preformed, granular structure, they are not to be optimally implanted into the osseous defects. This applies in particular in dentistry because of the lack of space in the oral cavity, where preformed bone replacement is to be positioned only with great difficulty. A further disadvantage of these sometimes sintered materials is that although they are integrated as bone, they are not completely degraded and replaced by natural bone.

For some time, calcium phosphate-containing powders have also been used, which are present initially as a paste after being admixed with water or aqueous solutions and then cure after a certain time. After curing, these materials display a structural similarity to the mineral phase of natural bone in the x-ray diffractogram. There are thus no longer problems with the adaptation to bone defects of the patient, as the pastes exactly match the existing structures.

Disadvantages occur, with the paste-based implants which have become known according to the state of the art, in the curing times, resistance to liquids acting from the outside, strength after curing, tissue integration as well as biodegradability. These matters are discussed below, in the further description of the state of the art.

One of the first powder- or paste-based implants is the BoneSource® invented by Brown and Chow in 1965, in which the powder component consists of $CaHPO_4$ and tetracalcium phosphate. After admixing with water, a curing cement paste results, the cured end-product of which is a nano-crystalline hydroxyl apatite with a calcium/phosphorous ratio (Ca/P) of 1.67 (i.e. 1.67 calcium atoms per phosphorous atom). A disadvantage of such a calcium phosphate cement is its relatively long curing period and the disadvantageous property of decomposing in the early phase of setting when in direct contact with liquids. This applies in particular in the case of direct introduction into bleeding bone wounds.

In the publication by Driessens et al, Bioceramics Vol 9, 1996, pages 231–234, amorphous calcium phosphate cements are described, the calcium/phosphorous ratio of which (Ca/P) is<1. These cements consist of $Ca(H_2PO_4)_2.H_2O$=mono-calcium phosphate monohydrate (MCPM) and $CaKPO_4$ or mixtures of MCPM and $Ca_2NaK(PO_4)_2$. As a result of their relatively high solubility in body fluids, they have lower compressive strengths than the previously described cements with a high Ca/P ratio. The reduced compressive strength is a disadvantage of these implant materials.

On the other hand, a degree, albeit small, of solubility of such materials in the body fluids is desired, as the materials can then be opened up more quickly by body cells, compared with cements which are insoluble in human or in animal body fluids and must essentially be described as osteotransductive.

The system comprising MCPM and $CaKPO_4$, apart from the disadvantage of its low compressive strength after curing, also has the disadvantage that its working time is less than 3 minutes.

This working time is clearly to short for difficult implant operations. The MCPM and $Ca_2NaK(PO_4)_2$ system also mentioned has higher compressive strengths, but the curing period is clearly too long compared with the system comprising MCPM and $CaKPO_4$.

Such cement systems and the products which result from them after curing, such as $Ca(H_2PO_4)_2.H_2O$ (=MCPM), hydroxyl apatite $Ca_{10}(PO_4)_8(OH)_2$ and others are known from patents U.S. Pat. Nos. 4,673,355, 5,053,212 or EP 0543765. The resorbability of these materials as well as the curing period are, as mentioned, still not satisfactory however.

For this reason, the object of the invention is to develop new implantable compositions with which curable, calcium phosphate-containing pastes can be admixed. Improved biological properties were important for the clinical success in patients, but also more favourable handling properties for the doctor providing treatment e.g. as regards the curing time. The composition according to the invention fulfils these conditions in an ideal manner.

It offers in particular the following advantages:

As it can be admixed to produce curing pastes, the result is an ideal adaptability to the existing bone structure in the patient.

Through variation of the composition, the curing time can be changed, which is extraordinarily advantageous during use.

During curing, the composition is resistant to liquids acting from outside, such as e.g. blood, which can occur with bleeding bone wounds.

After the implant paste has cured, a high initial strength of the implant very quickly results.

The tissue integration can be considerably accelerated by additives.

The special type of composition leads to a good biological degradability, the speed of which can be influenced by the added additives.

In the case of the implants corresponding to the state of the art, these positive properties are not present in combination with each other, so that the composition according to the invention represents a considerable technical advance.

The implantable composition according to the invention is characterized in that it contains a base mixture of (a) $CaKPO_4$
(b) $Ca_2NaK(PO_4)_2$ and
(c) $Ca(H_2PO_4)_2.H_2O$ The combination of (a), (b) and (c) referred to as base mixture is present in particular in the form of a powder mixture.

The subject of the present invention is furthermore the combination of suitable mixtures of calcium- and phosphorous-containing powders with different powdery additives and admixing liquids which consist of water or aqueous solutions with various additives.

The main feature of the calcium- and phosphorous-containing powder mixtures according to the invention is that they contain as essential component special mixtures of $CaKPO_4$, $Ca_2NaK(PO_4)_2$ and $Ca(H_2PO_4)_2.H_2O$ (=MCPM) which are designated base mixtures. Further calcium phosphate-containing powders are preferably added to these base mixtures. The admixing of other substances is however also possible. The afore mentioned disadvantages with the cement systems corresponding to the state of the art are avoided with the compositions according to the invention.

A preferred powder mixture of the composition according to the invention consists of the base mixture with addition of $CaHPO_4.H_2O$ and/or $CaCO_3$, further variable proportions of other calcium phosphate-containing substances and other additives being able to be added. By varying the quantity ratios of the individually named components, the properties of the composition according to the invention can be changed over a wide range and thus be adapted to the respective need.

Furthermore, the composition according to the invention preferably contains an admixing liquid which can in particular contain water. With this liquid the composition can be processed to a paste which is applied to the substrate to be treated, moulded and finally cured.

The admixing liquids used for admixing and curing can, as mentioned, contain additives with which the positive properties of the composition can also be decisively influenced. This applies e.g. as regards the biological accessibility of the cured cement for the body's own cells, as the tissue integration depends quite essentially on this.

The admixing liquid contains an aqueous solution of mannose-6-phosphate (M-6-P) in a preferred formulation. In the case of some formulations, it is also provided that saccharose-octasulphate is added to the admixing liquid. Mixtures of mannose-6-phosphate and saccharose-octasulphate in the admixing liquid are also provided for. The two named substances can however also be added to the powder component in certain formulations. In a preferred formulation, the saccharose-octasulphate is used as sodium or potassium complex salt.

It is also possible that antibiotics and disinfectants are added to the admixing liquid so that infections do not occur as long as the implant is not yet integrated into the tissue. Through the implantation of initially still unactivated calcium phosphate cement, there is always the risk of colonization by germs, as the cement is not yet resorbed and/or opened up in cellular or vascular manner. There is therefore a justified demand on the part of the user to provide such materials with substances which inhibit colonization by germs, or, by release of germ-inhibiting or—destroying active ingredients into the surroundings of the implant, protect the latter from the colonization by germs, or to treat the surroundings by releasing medicaments along the lines of a drug delivery system or active ingredient reservoir.

This is achieved by adding antibiotics or other germ-inhibiting and/or—destroying substances such as e.g. biguanide (e.g. chlorohexidine) to the cement powder. The antibiotics and/or disinfectants can however also be added to the admixing liquid which is used for curing the cement powder.

It is also possible to use as admixing liquids antibiotics-containing or disinfecting aqueous solutions such as are also commercially available. In this context, the following substances are preferably used:

Gentamicin containing injection solutions such as e.g. Duragentamicin 80 and Duragentamicin 160 (from Durachemie), tobramycin solutions or clindamycin-containing solutions such as e.g. Sobelin Solubile 300, 600 and 900 mg, or metronidazole-containing solutions such as e.g. Clont i.v. (from Bayer) or also metronidazole i.v. (from Braun). A Lavasept solution (from Fresenius) prepared with NaCl is also suitable as a disinfecting solution.

The composition according to the invention has the advantage that the curing speed and the compressive strength of the cured composition can be influenced in the desired way in particular by varying the quantity ratios of $CaKPO_4$ and $Ca_2NaK(PO_4)_2$ together with MCPM and, if present, $CaHPO_4.H_2O$. High proportions of $CaKPO_4$ and MCPM result in short curing times with a somewhat lower compressive strength. Conversely, a greater compressive strength can be achieved by higher proportions of $Ca_2NaK(PO_4)_2$ and MCPM, somewhat longer curing times then resulting.

Further possibilities for influencing the system properties result from the addition of variable proportions of $CaCO_3$ and/or nanoparticular apatite (corresponding to EP 0 664 133 A1). Higher proportions of nanoparticular hydroxyl apatite give the desired good biological degradability of the cured composition in the patients' body. Higher proportions of $CaCO_3$ lead to a high strength after curing, the curing time being somewhat lengthened.

Further, it was shown that the curing speed of the powder/liquid mixture clearly increases through the addition of aqueous $Na_2HPO_4$ solution with concentrations of in particular up to 5%, so that the operator has the possibility of selecting a curing speed which is optimal for the present case.

It emerges from the publication by Martinez et al, J-Cell-Biochem, 59(2), 1995 that osteoblasts have a receptor for mannose-6-phosphate (M-6-P), the formation of bone by osteoblasts being stimulated by intracellular signal transmission. An improved fracture healing in rabbits through the administration of saccharose octasulphate was reported by Young et al., Invest. Radiol. 26(5), 1991. The saccharose octasulphate is said to act via the binding of locally present growth factors such as EGF and FGF (Szabo et al., Scand-J-Gastroenterol, 185, 1991) and/or stimulation of the endogenous prostaglandin system (Stern et al, Am-J-Med, 83(3B), 1987). The positive effect of the saccharose octasulphate on bone growth was however not yet mentioned previously in the literature in connection with reaction systems for bone replacement. To this extent, the addition of this substance to the composition according to the invention is a preferred version.

A further important feature of the present invention relates to the combination of M-6-P and saccharose octasulphate as additives for the base mixture ($CaKPO_4$, $Ca_2NaK(PO_4)_2$, MCPM) in combination with $CaHPO_4 \cdot H_2O$ and $CaCO_3$. The saccharose octasulphate can be introduced into the cement in the form of an aqueous solution as a liquid component or added in powder form to the mineral powder component. In this way, the object of preparing a calcium phosphate cement with the mentioned user-optimized curing properties and good strength after curing, which at the same time has the ability to bind growth factors, is achieved.

A cellular opening up of the implant via the formation of new blood vessels is thereby made possible. In addition, osteoblasts for the formation of new bones are also stimulated.

Through this combination, an intensified biological activity and thus also a resorbability of the synthetic bone replacement material is achieved. Resistance to liquids such as e.g. blood results from the cohesion of the components used.

Mixtures with the following relative weight proportions have proved to be particularly suitable formulations for the base mixture ($CaKPO_4$, $Ca_2NaK(PO_4)_2$ and MCPM):

The proportion of $CaKPO_4$ and $Ca_2NaK(PO_4)_2$ in the overall base mixture lies between 80% and 65%.

The proportion of MCPM is accordingly 20% to 35%

The ratio of $CaKPO_4$ to $Ca_2NaK(PO_4)_2$, relative to the overall quantity of these two substances, can vary within wide limits. Thus the proportion of $CaKPO_4$ can lie between 1% and 99%, the proportion of $Ca_2NaK(PO_4)_2$ accordingly lying between 99% and 1%.

It is preferable to use the three substances of the base mixture in an approximate molar ratio of 2 mol $CaKPO_4$, 1 mol $Ca_2NaK(PO_4)_2$ and 1 mol MCPM.

The preparation of the two components $CaKPO_4$ and $Ca_2NaK(PO_4)_2$ used for the reaction system according to the invention is carried out in particular as described hereafter.

Preparation of $CaKPO_4$

Firstly, 1 mol $K_2CO_3$ is mixed with 2 mols $CaHPO_4$ and the powder mixture is calcined for approx. 1 hour at 1000° C. A rapid cooling to temperatures <700° C. follows the calcination. The cooling period must not be greater than 1 minute.

Preparation of $Ca_2NaK(PO_4)_2$

The $Ca_2NaK(PO_4)_2$ is prepared analogously to the $CaKPO_4$, i.e. the same process parameters are used for calcination and cooling. The powder mixture before calcination consists of 1 mol $K_2CO_3$, 1 mol $Na_2CO_3$ and 4 mols $CaHPO_4$.

It is preferable that the components $CaKPO_4$ and $Ca_2NaK(PO_4)_2$ contained in the composition according to the invention are calcined at 1000° C. and then brought by rapid cooling to less than 700° C. within 1 minute.

To further improve the biological properties of the composition according to the invention, biologically active proteins such as growth factors can be added both to the powder mixtures and to the admixing liquids. Fibroblast growth factor (FGF), bone morphogenetic proteins (BMPs), enamel amelogenins or elastase inhibitors such as e.g. AEBSF (P 2714 from Sigma) can be considered for example. Bone morphogenetic proteins are substances which influence the protein metabolism upon the synthesis of new tissue in the direction of a particular structure class, in this case in the direction of bone growth. Enamel amelogenins are likewise bone morphogenetic proteins which are responsible in particular for the growth of the periodontal apparatus.

The compositions according to the invention comprising powder mixtures and admixing liquids produce implantation pastes which set at both room and body temperature.

The cured implantation pastes have compressive strengths which depend on their composition and can be more than 5 MPa. They are characterized by a curing time which can be set by the user within wide limits. A preferred embodiment is the use of a powder mixture according to example 2, by which the development of the material, initially inanimate in cellular terms, is very positively influenced by cells of the human or animal body.

The invention relates, finally, to the use of the composition to repair or replace bones, teeth or parts thereof. In particular, the procedure is such that the composition is applied to the selected substrate in the form of a paste, moulded and cured.

Various formulations have proved to be particularly advantageous for the different applications. In the following, some of the particularly advantageous formulations are described in examples 1 to 10. However, other formulations are also provided for.

EXAMPLE 1

Base mixture consisting of 13.92 g $CaKPO_4$ and 19.93 g $Ca_2NaK(PO_4)_2$ (corresponds respectively to 41.1 wt.-% and 58.9 wt.-% of the mixture of the two substances) and 10.41 g $Ca(H_2PO_4) \cdot H_2O$ (=MCPM) (corresponds to 23.5 wt.-% MCPM of the overall quantity of the base mixture).

The powder mixture is mixed intensively, a pre-grinding of the individual powder components taking place in a ball mill. The curing characteristic of the cement mixture results as follows after the admixing of 2 g powder with 1 ml water according to ASTM C266-89 (standard for determining the solidification of glue, cement and plaster):

1. Curing time ($1^{st}$ c.t.), measured with the light Gillmore needle, after 4 minutes 5 seconds.
2. Curing time ($2^{nd}$ c.t.), measured with a heavy Gillmore needle, after 8 minutes 40 seconds.

With the formulation described above and the same powder/liquid ratio, cylindrical test pieces measuring 6 mm in diameter×12 mm in height reach a compressive strength of 10.6 MPa after 24 hours' incubation in Ringer's solution.

This composition thus shows a very good reaction time upon curing and gives good compressive strengths.

EXAMPLE 2

Base mixture prepared as described in example 1. However, 1 ml of an aqueous solution of 5 mMol mannose-6-phosphate (M-6-P) from Sigma which also contains 100 μg saccharose octasulfate per 1 ml, on 2 g powder, is used as admixing liquid for the preparation of an implantable paste.

The first c.t. is 4 minutes in this case, and the second c.t. 8 minutes 10 seconds.

EXAMPLE 3

In addition to the powder mixtures shown in examples 1 and 2 and described previously, further mixtures comprising the base mixture ($CaKPO_4$, $Ca_2NaK(PO_4)_2$ and MCPM) as well as $CaHPO_4.H_2O$, $CaCO_3$ and $CaHPO_4$ are proposed. Combinations of the base mixture with additions of $CaHPO_4.H_2O$ in quantities of 1 to 60 wt.-%, relative to the overall powder quantity, or additions of $CaCO_3$ in quantities of 1 to 60 wt.-%, relative to the overall powder quantity, proved to be particularly suitable powder mixtures.

The admixing of combinations of $CaHPO_4.H_2O$ and $CaCO_3$ to the base mixture is also advantageous, the proportion in percentages by weight of $CaHPO_4.H_2O$ between 1% and 30%, and the proportion of $CaCO_3$ lying between 30% and 1%, relative to the overall mixture.

EXAMPLE 4

Mixture of the following composition: base mixture consisting of: 13.92 g $CaKPO_4$+19.93 g $Ca_2NaK(PO_4)_2$+10.41 g MCPM with the addition of 11.5 g $CaHPO_4.H_2O$.

The components named are mixed in a ball mill and ground. Upon admixing of 2 g of this powder with 0.9 ml water, a first c.t. of 4 minutes 30 seconds results and a second c.t. of 11 minutes 15 seconds.

The paste can also be admixed with 0.9 ml of an aqueous, 2-% $Na_2HPO_4$ solution instead of water. The first c.t. is then 2 minutes 45 seconds and the second c.t. 7 minutes 25 seconds.

By addition of $CaHPO_4.H_2O$ (DCPD), the compressive strength of a test cylinder (see example 1) is increased to 16 MPa. This is a clearly higher value than mentioned in example 1, in which the formulation was given without $CaHPO_4.H_2O$.

EXAMPLE 5

In this case, a powder similar to that described in example 4 is involved. Instead of $CaHPO_4.H_2O$ (DCPD), however, its anhydride ($CaHPO_4$) is used, the other components remaining the same.

Upon admixing of 2 g of the powder with 0.9 ml of an aqueous 2-% $Na_2HPO_4$ solution, the same curing times are achieved as described under example 4, but the compressive strength falls to 6.9 MPa (measured as described in example 1).

EXAMPLE 6

This involves a powder mixture as described in example 1, with an addition of 10% $CaCO_3$.

The first c.t. is 2 minutes, the second c.t. is 7 minutes 45 seconds. The compressive strength is 7.3 MPa after incubation in Ringer's solution over 24 hours at 37° C.

EXAMPLE 7

This formulation involves a powder mixture as described in example 1, but with the further addition of 6 g $CaHPO_4.H_2O$ and 6 g $CaCO_3$. After admixing of 2 g of the powder with 1 ml water, a first c.t. of 6 minutes 30 seconds results and a second c.t. of 12 minutes.

Using the same powder mixture, but with a 4-% $Na_2HPO_4$ solution instead of the water, a first c.t. of 3 minutes 30 seconds and a second c.t. of 9 minutes 15 seconds is obtained.

EXAMPLE 8

In this formulation, 2 g powder mixture having a composition according to example 1 are admixed with 1 ml Sobelin Solubile 600 mg solution. The curing times are somewhat extended compared with the times named in example 1. The first c.t. is 6 minutes 30 seconds and the second c.t. is 13 minutes.

EXAMPLE 9

In this formulation, 2 g powder mixture having a composition according to example 1, are admixed with 1 ml Duragentamicin 160 mg solution. The admixing results after only 15 seconds in a paste of good consistency which no longer leads to demixing or softening upon contact with further liquid. The curing times are unchanged compared with example 1.

EXAMPLE 10

In this formulation, 2 g powder mixture having a composition according to example 1, are mixed with 1 ml Clont i.v. infusion solution (from Bayer). Only 15 seconds after the beginning of the admixing, a firmly-adhering paste is obtained which no longer disperses on contact with water. The curing times are somewhat shorter compared with example 1. The first c.t. is 3 minutes 55 seconds and the second c.t. is 8 minutes.

What is claimed is:

1. Implantable composition which comprises a base mixture of 80 to 65 wt.-% of the combination of
   (a) $CaKPO_4$ and
   (b) $Ca_2NaK(PO_4)_2$ and 20 to 35 wt.-% of
   (c) $Ca(H_2PO_4)_2.H_2O$.

2. Composition according to claim 1, in which, relative to the overall quantity of $CaKPO_4$ and $CaNaK(PO_4)_2$, the proportion by weight of $CaKPO_4$ lies between 1% and 99% and that of $CaNaK(PO_4)_2$ between 99% and 1%.

3. Composition according to claim 1, in which the base mixture is present in the form of a powder mixture.

4. Composition according to claim 1, which in addition comprises at least one of the following components:
   $CaHPO_4.H_2O$, $CaCO_3$, $CaSO_4$, $CaSO_4.O.5H_2O$, $CaSO_42H_2O$,
   $CaHPO_4$, nanoparticular hydroxylapatite.

5. Composition according to claim 1, which comprises a powder mixture of the base mixture with addition of $CaHPO_4.H_2O$ and $CaCO_3$ and wherein, relative to the powder mixture, the proportion by weight of $CaHPO_4.H_2O$ lies between 1% and 30% and the proportion by weight of $CaCO_3$ between 30% and 1%.

6. Composition according to claim 1, which comprises a powder mixture of the base mixture with addition of $CaHPO_4.H_2O$ and wherein, relative to the powder mixture, the proportion by weight of $CaHPO_4.H_2O$ lies between 1% and 60%.

7. Composition according to claim 1, which comprises a powder mixture of the base mixture with addition of $CaCO_3$ and wherein, relative to the powder mixture, the proportion by weight of $CaCO_3$ lies between 1% and 60%.

8. Composition according to claim 1, which also comprises at least one of the following components:

mannose-6-phosphate, saccharose-octasulphate, saccharose-octasulphate in the form of the sodium or potassium complex salt, an antibiotic and a disinfectant.

9. Composition according to claim 1, which also comprises an admixing liquid.

10. Composition according to claim 9, in which the admixing liquid contains water.

11. Composition according to claim 9, which is present in the form of a paste.

12. Composition according to claim 9, in which the admixing liquid comprises an aqueous solution of mannose-6-phosphate, of saccharose-octasulphate or of a mixture of these.

13. Composition according to claim 9, in which the admixing liquid comprises an aqueous solution of $Na_2HPO_4$.

14. Composition according to claim 9, in which the admixing liquid comprises at least one of the following components mannose-6-phosphate, saccharose-octasulphate, saccharose-octasulphate in the form of the sodium or potassium complex salt, an antibiotic and a disinfectant.

15. Composition according to claim 1, which also comprises biologically active proteins.

16. Composition according to claim 15, which comprises, as biologically active proteins, growth factors, bone morphogenetic proteins, enamel amelogenins and/or elastase inhibitors.

17. A method for the repair or replacement of bones, teeth or parts thereof comprising applying a composition according to claim 1 to a bone, tooth or parts thereof in need of repair.

18. The method according to claim 17, which the composition is applied to the selected substrate in the form of a paste, moulded and cured.

* * * * *